(12) United States Patent
Annis et al.

(10) Patent No.: US 6,628,745 B1
(45) Date of Patent: Sep. 30, 2003

(54) IMAGING WITH DIGITAL TOMOGRAPHY AND A RAPIDLY MOVING X-RAY SOURCE

(76) Inventors: Martin Annis, 65 Banks St., Cambridge, MA (US) 02138; Richard Adler, 9131 Mabry Ave., NE., Albuquerque, NM (US) 87101

( * ) Notice: Subject to any disclaimer, the term of this patent is extended or adjusted under 35 U.S.C. 154(b) by 0 days.

(21) Appl. No.: 09/897,715

(22) Filed: Jul. 2, 2001

Related U.S. Application Data
(60) Provisional application No. 60/215,665, filed on Jul. 1, 2000, and provisional application No. 60/218,957, filed on Jul. 17, 2000.

(51) Int. Cl.[7] .................................................. A61B 6/00
(52) U.S. Cl. .............................. 378/21; 378/10; 378/57; 378/143; 378/26; 378/62
(58) Field of Search ............................... 378/57, 21, 20, 378/19, 12, 10, 14, 22, 143, 137, 138, 62, 26

(56) References Cited

U.S. PATENT DOCUMENTS

| | | | | |
|---|---|---|---|---|
| 4,352,021 A | * | 9/1982 | Boyd et al. | 378/10 |
| 4,521,901 A | * | 6/1985 | Rand | 378/12 |
| 4,989,225 A | * | 1/1991 | Gupta et al. | 378/10 |
| 5,119,408 A | * | 6/1992 | Little et al. | 378/10 |
| 5,199,054 A | * | 3/1993 | Adams et al. | 378/21 |
| 5,583,904 A | * | 12/1996 | Adams | 378/22 |
| 6,236,709 B1 | * | 5/2001 | Perry et al. | 378/25 |
| 6,324,249 B1 | * | 11/2001 | Fazzio | 378/22 |
| 6,501,822 B2 | * | 12/2002 | Roder | 378/22 |

* cited by examiner

*Primary Examiner*—Drew A. Dunn
*Assistant Examiner*—Jurie Yun
(74) *Attorney, Agent, or Firm*—Inna Landsman

(57) ABSTRACT

A digital tomography system includes an electron source that provides a beam of electrons, and an electromagnet assembly that receives said beam of electrons and is configured and arranged to direct the beam of electrons along a selected path, wherein the assembly provides a redirected beam of electrons. The system also includes a target that is struck by the redirected beam of electrons and generates a cone of x-rays, and a slit collimator that receives the cone of x-rays and generates a fan beam. A first line of detectors is positioned to detect x-rays that pass through the object under inspection, and provide sensed signals indicative thereof to a controller that receives the sensed signals and forms a displayable image of a selected plane through the object under inspection.

14 Claims, 19 Drawing Sheets

END VIEW

IMAGING WITH DIGITAL TOMOGRAPHY AND A RAPIDLY MOVING X-RAY SOURCE

CROSS REFERENCE TO RELATED APPLICATIONS

This application claims priority from the provisional application designated Ser. No. 60/215,665 filed Jul. 1, 2000 and entitled "Imaging With Digital Tomography and a Rapidly Moving X-Ray Source", and the provisional application designated Ser. No. 60/218,957 filed Jul. 17, 2000 and entitled "Imaging With Digital Tomography and a Rapidly Moving X-Ray Source". Both applications are hereby incorporated by reference.

BACKGROUND OF THE INVENTION

The invention relates to the field of x-ray imaging systems, and in particular to an x-ray imaging system that employs digital tomography and a rapidly moving x-ray source.

DETAILED DESCRIPTION OF THE INVENTION

The original tomography systems employed an imaging technique wherein an x-ray source and a film mounted below the object under inspection (typically a person) were moved in opposed directions along prescribed paths so that only one plane of the object under inspection is in focus at all times. The motion of the x-ray source is in a plane parallel to the plane of the film. Structures in a slice parallel to the film plane projected onto the film in the same relative positions throughout the entire examination. All other planes above and below projected in different positions of the film at different times through the motion, and therefore were blurred. This system allowed the production of only a single slice of the object under inspection with each exposure to the cone of x-rays.

With the development of scintillating materials, solid state detectors and digital computers, linear digital tomography systems were developed using an x-ray source and collimator emitting a fan beam of x-rays incident on a line of detectors. The fan beam is translated along the line of detectors by physically moving the source, and every detector is sampled as the fan beam translates. It is then possible to later choose the proper set of detectors to read which will focus on a single line, parallel to the line of detectors. Because all of the data is stored, this line can be chosen at any distance between the x-ray source and the line of detectors.

A limitation of this prior art technique is that the x-ray source must be moved mechanically, and therefore slowly in order to translate the beam along the line of detectors. Thus, each line of data requires mechanical motion of the rather heavy x-ray source along the full dimension of the object being imaged. For example, if the motion of the source were to be accomplished in 1 second, and if one wished to have an image with 1000 pixels in the direction perpendicular to this motion, it would take 1000 seconds to complete an image. In addition, the complexity of such a mechanical moving system is considerable.

Therefore, there is a need for a x-ray imaging system, such as for example a digital tomography system, which rapidly positions the x-ray beam without having to mechanically scan/move the x-ray source over the object under inspection.

SUMMARY OF THE INVENTION

Briefly, according to an aspect of the invention, a digital tomography system includes an electron source that provides a beam of electrons, and an electromagnet assembly that receives said beam of electrons and is configured and arranged to direct the beam of electrons along a selected path, wherein the assembly provides a redirected beam of electrons. The system also includes a target that is struck by the redirected beam of electrons and generates a cone of x-rays, and a slit collimator that receives the cone of x-rays and generates a fan beam. A first line of detectors is positioned to detect x-rays that pass through the object under inspection, and provide sensed signals indicative thereof to a controller that receives the sensed signals and forms a displayable image of a selected plane through the object under inspection.

The digital tomography system can be configured and arranged for various applications including for example, medical applications and for contraband detection. For example, in a medical application the electron source would be rather low energy, such as a 150 KeV x-ray tube. In a contraband detection suitable for the inspection of cargo pallets and trucks, the electron source would be a rather high energy source, such as for example greater than one MeV. In addition, the system may be configured either as a stationary system or as a mobile system (e.g., mounted on a truck).

These and other objects, features and advantages of the present invention will become more apparent in light of the following detailed description of preferred embodiments thereof, as illustrated in the accompanying drawings.

BRIEF DESCRIPTION OF THE DRAWINGS

FIG. 16 is a pictorial top view of the mobile digital tomography x-ray inspection system 250;

DETAILED DESCRIPTION OF THE INVENTION

Figure 1:
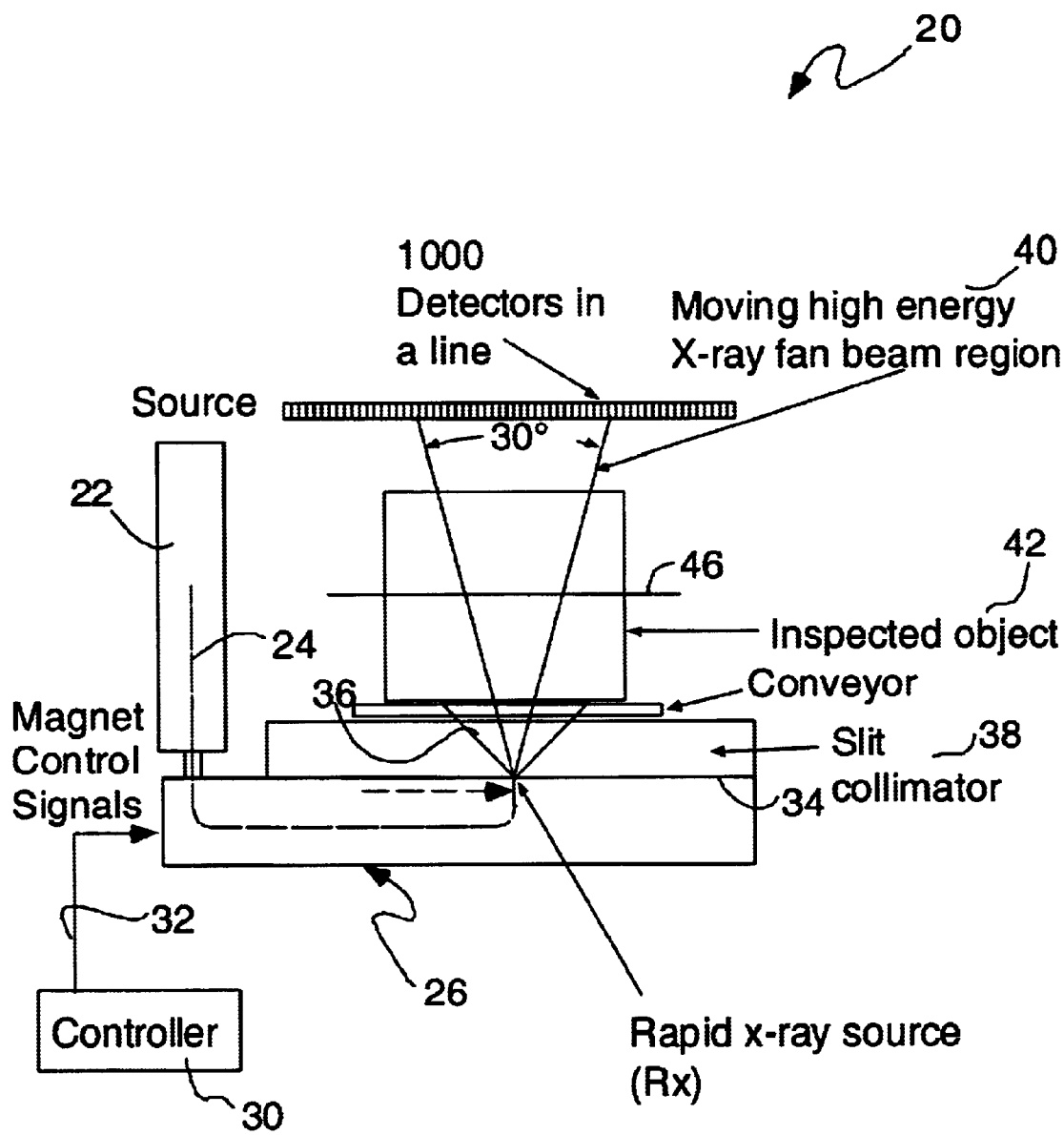
FIG. 1 is a pictorial illustration of an x-ray imaging system suitable for inspecting a cargo pallet.

FIG. 1 illustrates a digital tomography system 20 that includes a rapidly moving x-ray source 22. In one embodiment, the source 22 includes a high voltage electron accelerator, which is preferably a nested high voltage generator (NHVG) as disclosed in U.S. Pat. No. 5,124,658, incorporated herein by reference. It is contemplated that any other suitable electrostatic generator/accelerator may also be used. The type of source will depend of course on the type of object(s) the system is designed to inspect. For example, in a medical imaging application the source may be a relatively low energy source (e.g., about 150 KeV), while in a contraband detection system designed to inspect shipping container or trucks the source may be a relatively high energy source (e.g., greater than about 1 MeV).

The source 22 provides an electron beam 24 that enters a vacuum chamber 26, which includes an electromagnet assembly. Magnetic steering of an electron beam to generate a scanning x-ray beam is disclosed in U.S. Pat. No. 6,009,146, which is incorporated herein by reference. A controller 30 provides control signals on a line 32 to the electromagnet assembly to direct the electron beam 24 to strike a desired location on a target 34 (e.g., tungsten or gold) that emits a penetrating cone of x-rays 36. The cone of x-rays 36 from the target 34 enters a collimator 38 that includes a slit, from which an x-ray fan beam 40 exits and penetrates an object under inspection 42. X-rays that pass through the object under inspection 42 are detected by a line of detectors 44 (e.g., having 750 detectors spaced a known distance apart). To image a line of a desired horizontal plane 46 of the object under inspection 42, the electron beam 24 is scanned across the target 34 to generate the fan beam 40 that moves in a first direction (e.g., laterally), while the object under inspection 42 moves in a second perpendicular direction (e.g., longitudinally) along a moving conveyor.

Figure 2:
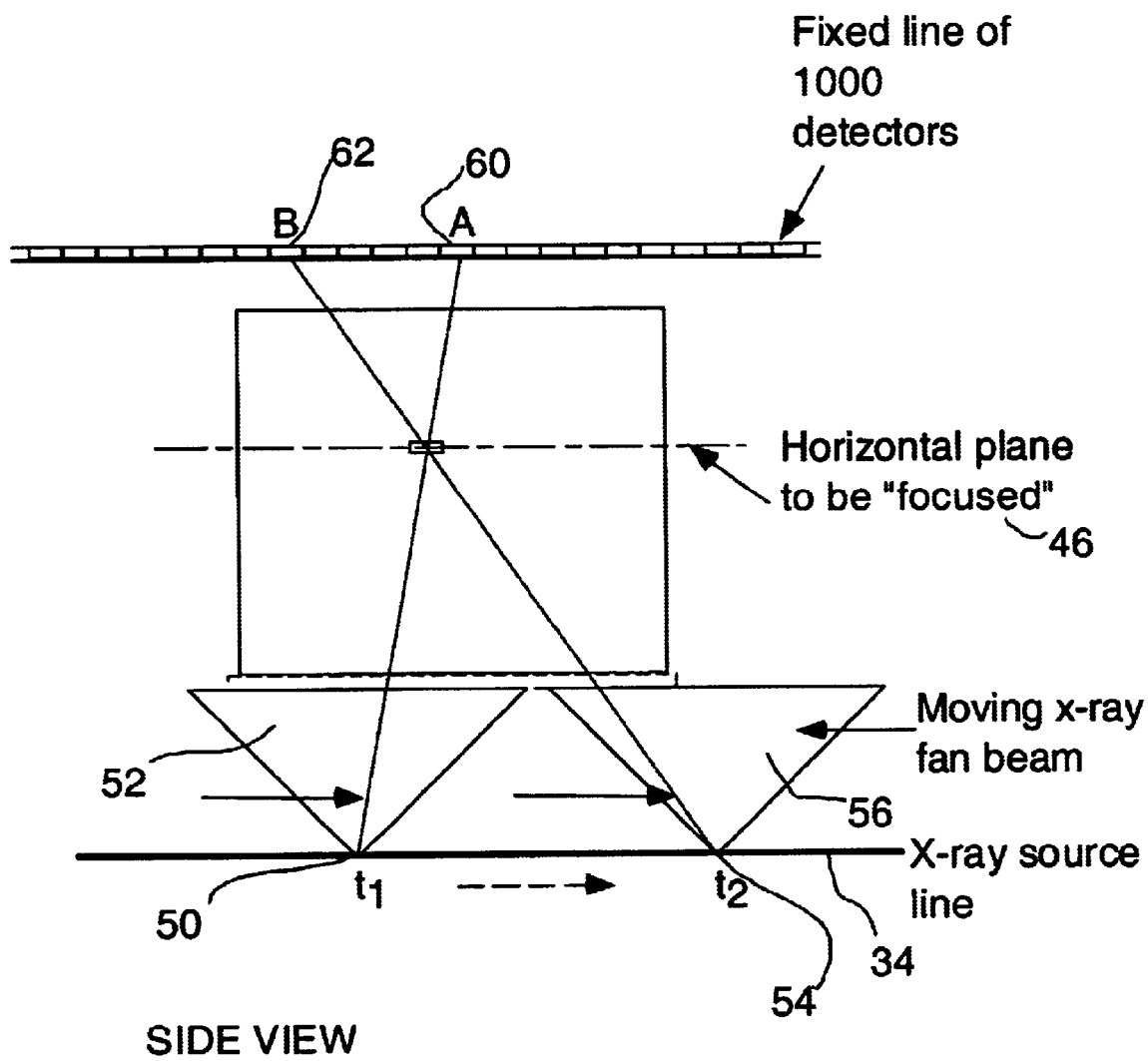
FIG. 2 is a pictorial illustration of the x-ray imaging system of FIG. 1 showing the fan beam position at times t1 and t2.

FIG. 2 illustrates how the fan beam is scanned and positioned at times t1 and t2. Specifically, at time t1 the electron beam strikes the target 34 at location 50 and generates the resultant cone of x-rays that is collimated to form a first fan beam 52. At time t2 the controller 30 (FIG. 1) provides magnet control signals on the line 32 (FIG. 1) that drive the electromagnetic assembly to direct the electron beam to strike the target at location 54. The resulting cone of x-rays is then collimated to form a second fan beam 56. At time t1, a first point 58 along the horizontal line 46 to be focused is imaged by detector A 60, and at time t2 the first point is imaged by detector B 62. Using known processing techniques an image of the desired horizontal plane 46 is generated.

Notably, the present invention rapidly scans the electron beam 24 (FIG. 1) to generate a scanning fan beam of x-rays, which is used to generate an image utilizing the principals of digital tomography.

Figure 3:
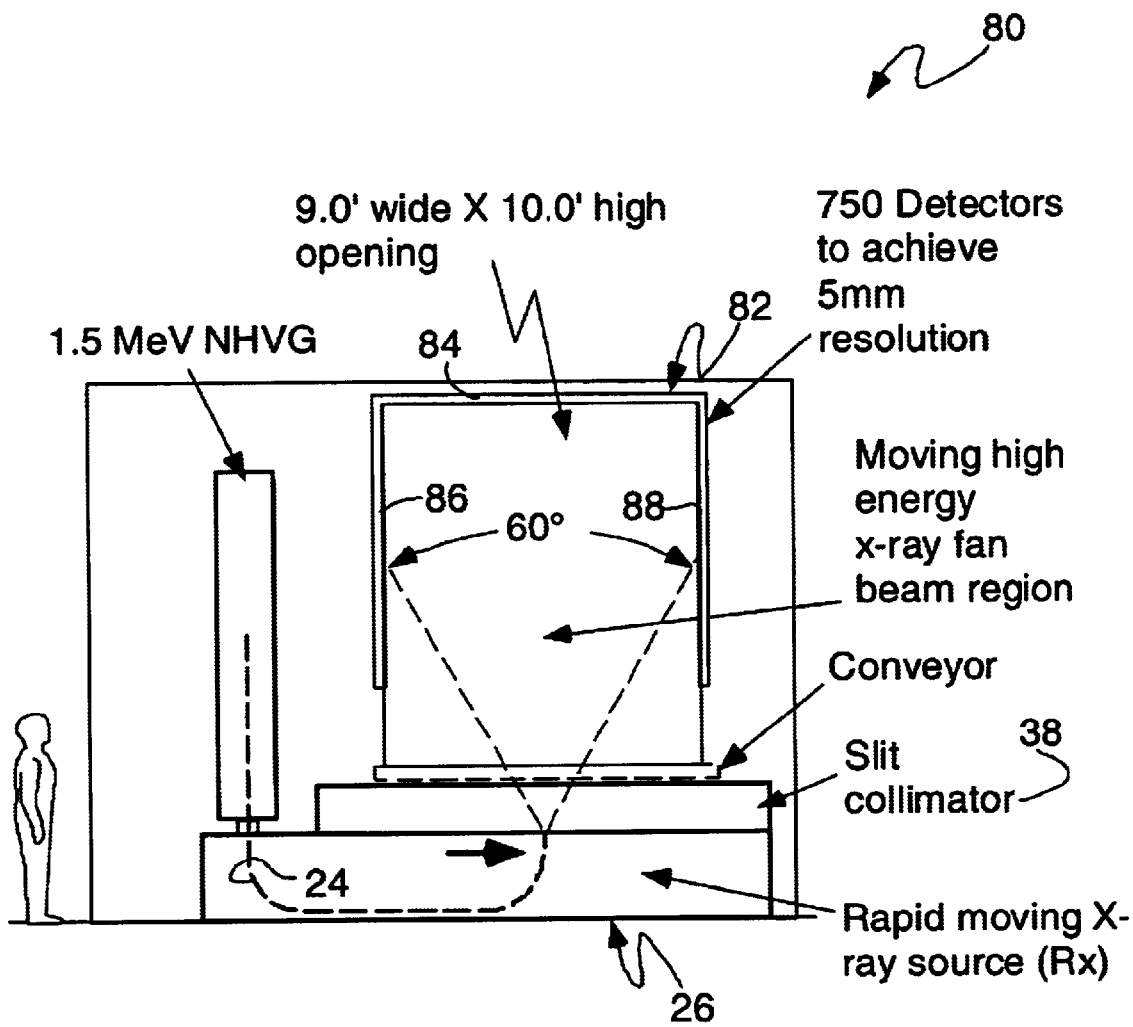
FIG. 3 is a pictorial illustration of an x-ray imaging system that includes a U-shaped detector.

FIG. 3 illustrates an alternative embodiment digital tomography system 80 that includes a U-shaped detector 82. The detector 82 includes a first line of detectors 84, a second line of detectors 86 and a third line of detectors 88. The second and third lines of detectors 86, 88 are each substantially perpendicular to the first line of detectors 84, and each line of detectors is configured and arranged to detect x-rays that pass through the object under inspection.

Figure 4:
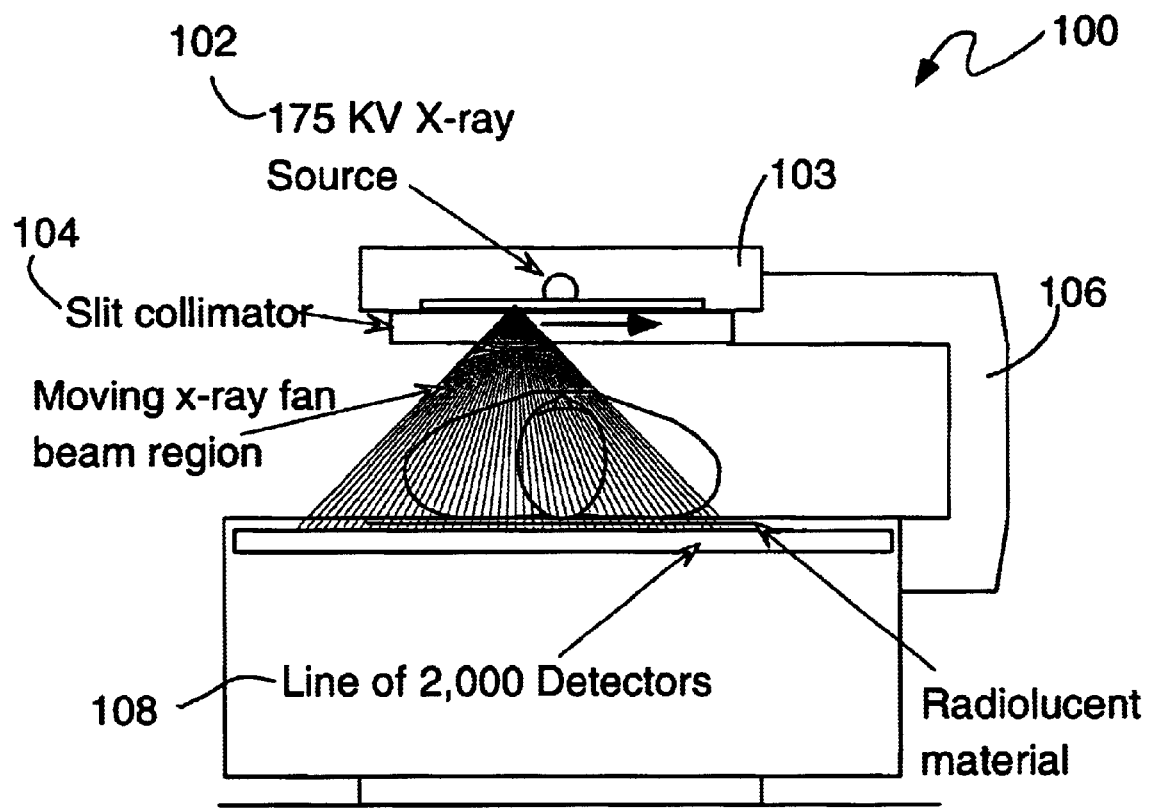
FIG. 4 illustrates an end view of a medical tomography imaging system.

FIG. 4 illustrates an end view of a medical tomography imaging system 100, suitable for quickly and inexpensively performing a full body scan of a patient (e.g., a trauma patient, such as a gun shot patient). This medical imaging system 100 employs a relatively low peak energy x-ray source 102, such as for example an x-ray tube (typically 160 kV). The x-ray source 102 provides an electron beam within a vacuum chamber 103 that includes electromagnet assembly, which deflects (i.e., scans) the electron beam along a target 105. The X-rays generated from the incident electrons striking the target are collimated by a slit 104 and laterally scanned along a patient. While the x-ray beam is laterally scanning along the patient, a boom 104 (e.g., a "C-shaped boom") that supports the x-ray source and a line of detectors 108 is scanned over the patient head-to-toe (or visa-versa). Alternatively, the patient may be placed on a moveable conveyor so the patient is scanned head-to-toe.

Figure 5:
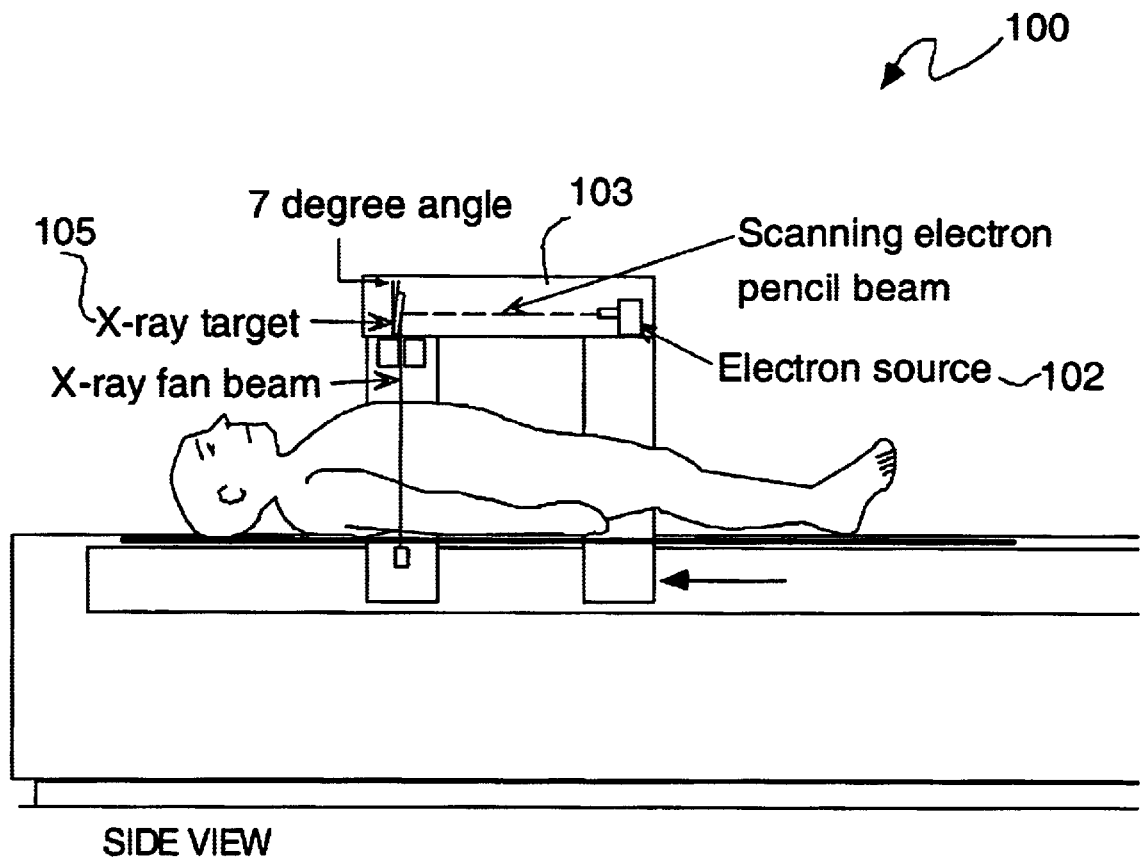
FIG. 5 illustrates a side view of the medical tomography system illustrated in FIG. 4.
Figure 6:
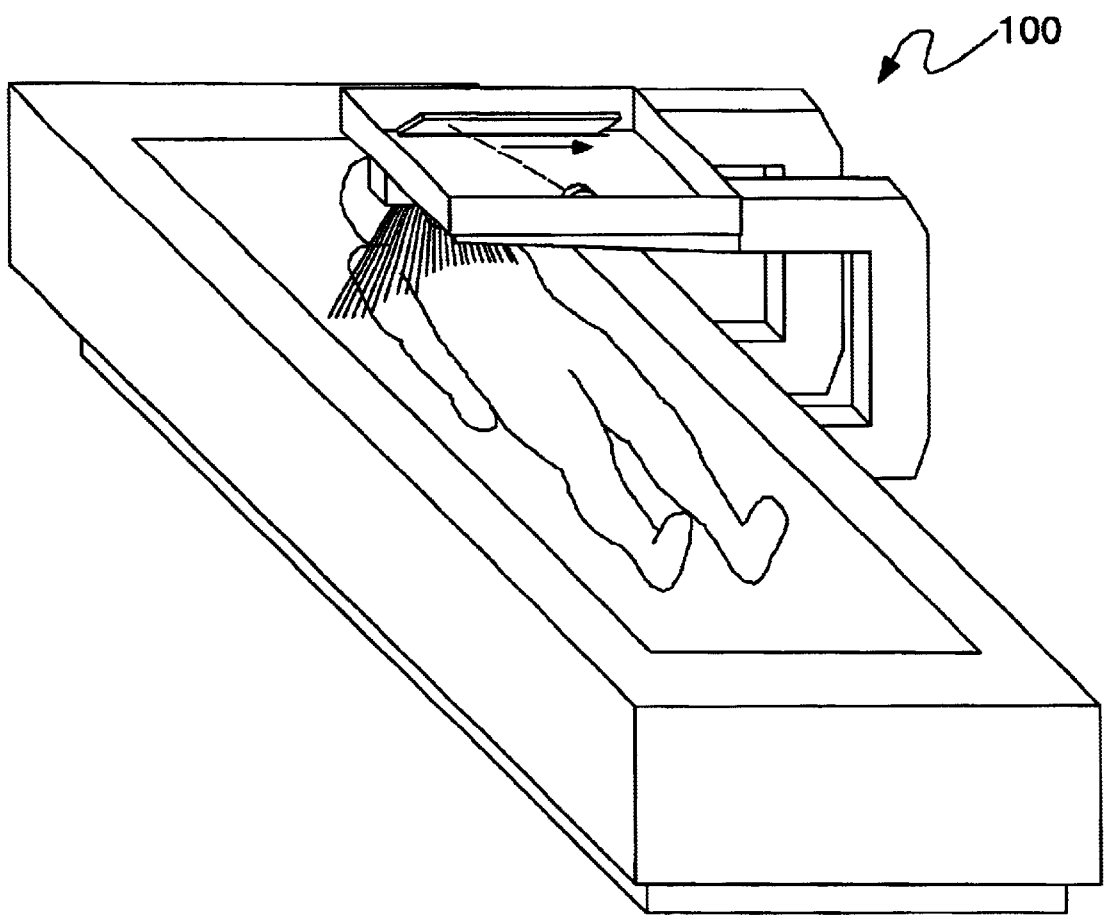
FIG. 6 illustrates a perspective view of the system illustrated in FIGS. 4 and 5.

FIG. 5 illustrates a side view of the medical tomography system 100, while FIG. 6 illustrates a perspective view of the system 100.

Figure 7:
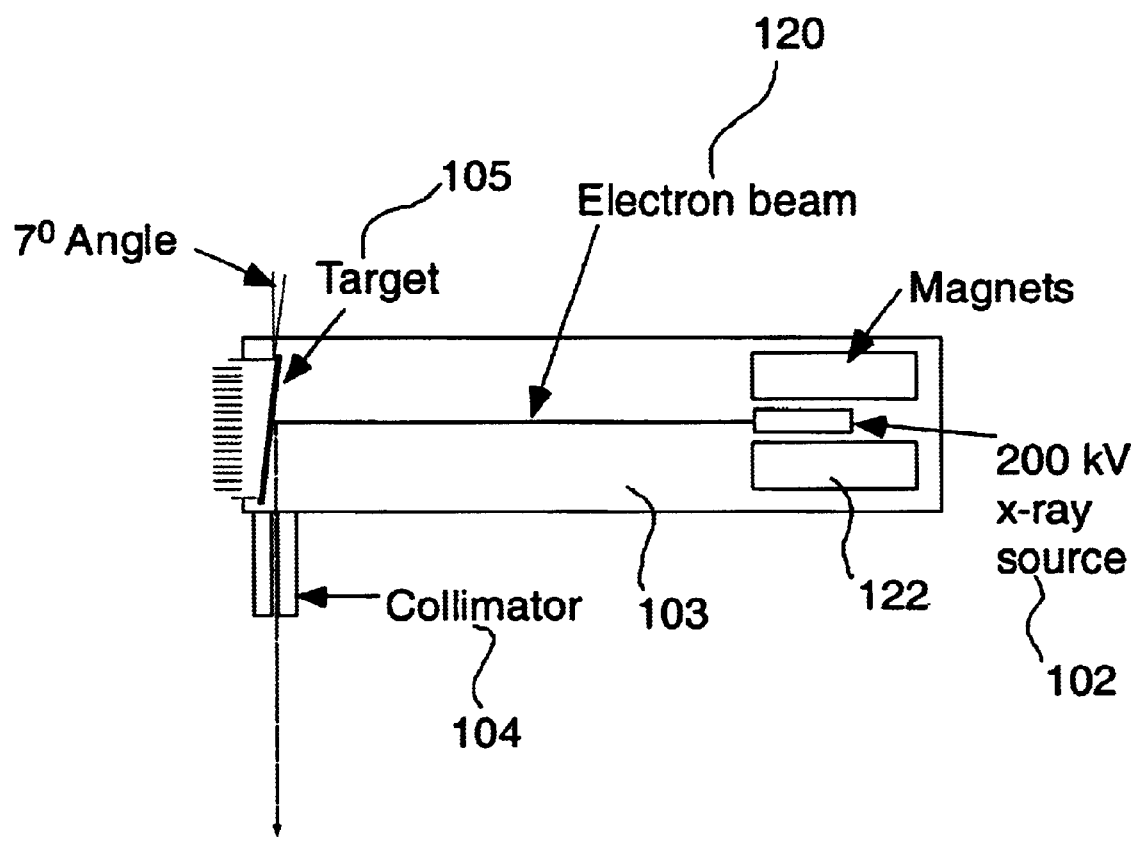
FIG. 7 is a pictorial illustration of the source, electromagnet assembly and the target 105 of the system illustrated in FIGS. 4–6.

FIG. 7 is a pictorial illustration of the source 102, electromagnet assembly and the target 105. Magnets 120, 122 receive control signals from the controller (FIG. 1). In this embodiment the target is preferably oriented at a 7 degree angle.

In an alternative medical tomography system embodiment, the source may be placed below the patient, and the detectors above the patient.

Figure 8:
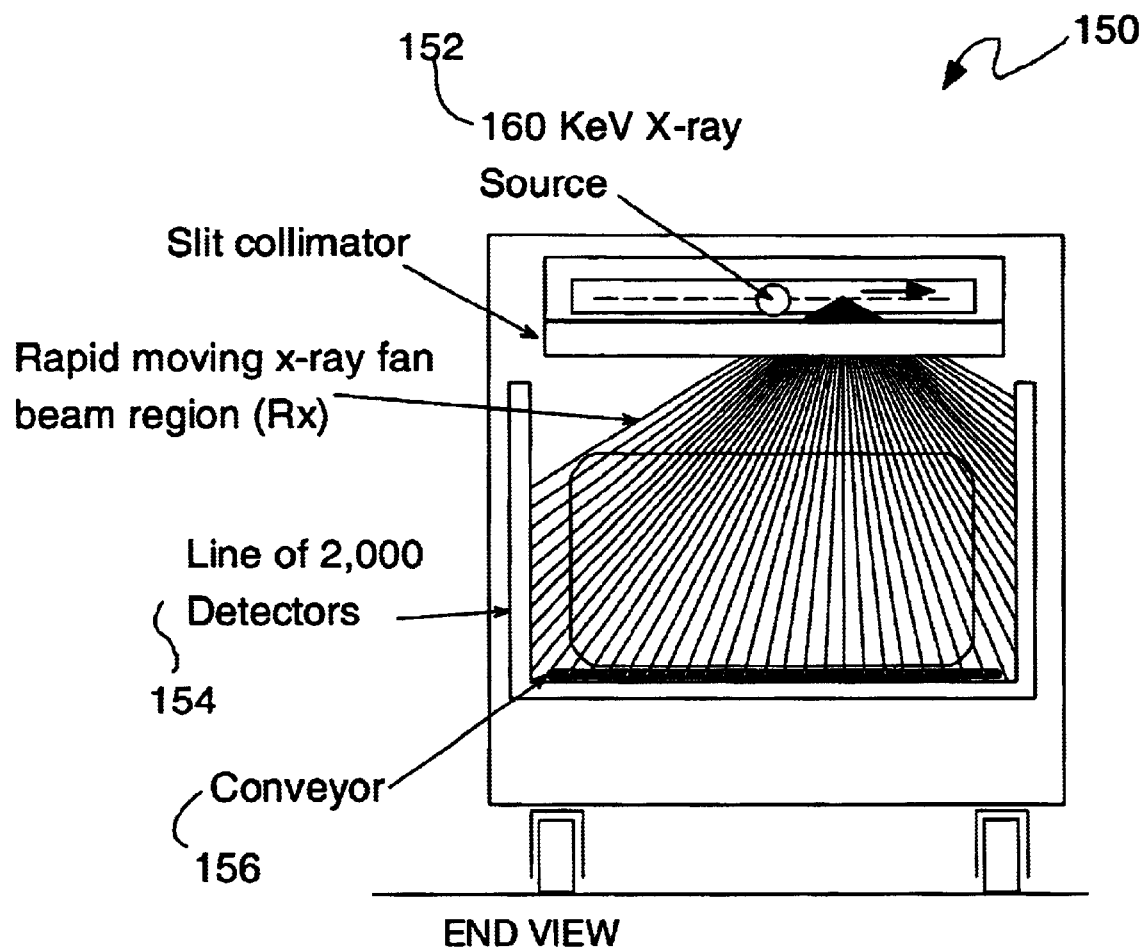
FIG. 8 illustrates a digital tomography x-ray inspection system for inspecting luggage.

FIG. 8 illustrates a digital tomography x-ray inspection system 150 for inspecting luggage. The system 150 includes an x-ray source 152 that provides an electron beam that is magnetically deflected to strike a target at a desired location. The electron beam is deflected to scan along the target, in order to scan a collimated x-ray beam (e.g., a fan beam). The system of course also includes a detector assembly 154, which is preferably configured and arranged as a U-shaped detector assembly. In order to scan the entire piece of luggage, the system includes a conveyor 156 that moves the luggage through the inspection system.

Figure 9:
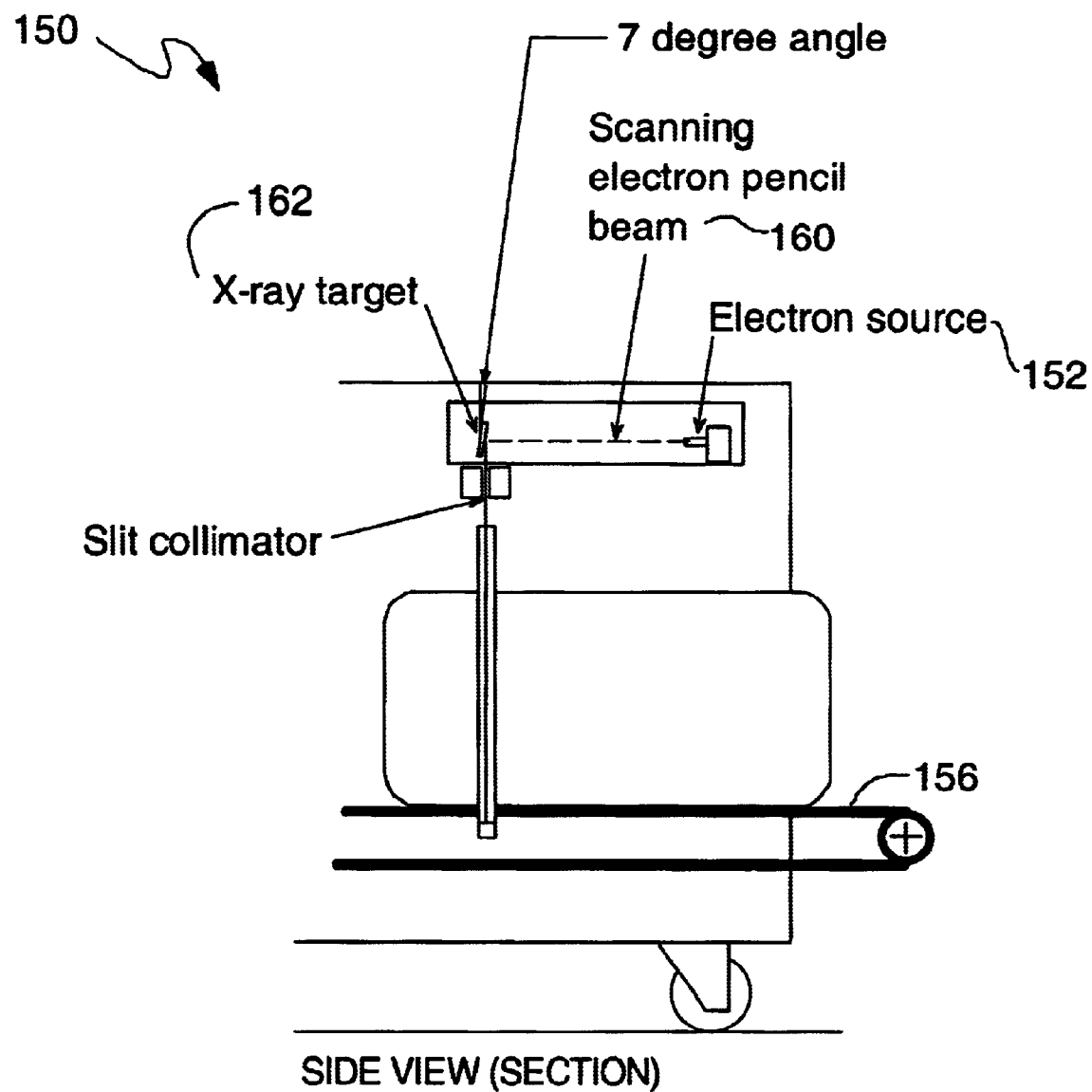
FIG. 9 is a pictorial illustration of a portion of a side view of the digital tomography x-ray inspection system illustrated in FIG. 8.

FIG. 9 is a pictorial illustration of a portion of a side view of the digital tomography x-ray inspection system 150. Similar to the system illustrated in FIG. 7, the source 152 generates electron beam 160, which is magnetically deflected to strike the target 162, generating a cone of x-rays that is collimated to form the fan beam. Of course in an alternative embodiment, the source may be placed below the piece of luggage under inspection, and the detectors above the piece of luggage.

Figure 10:
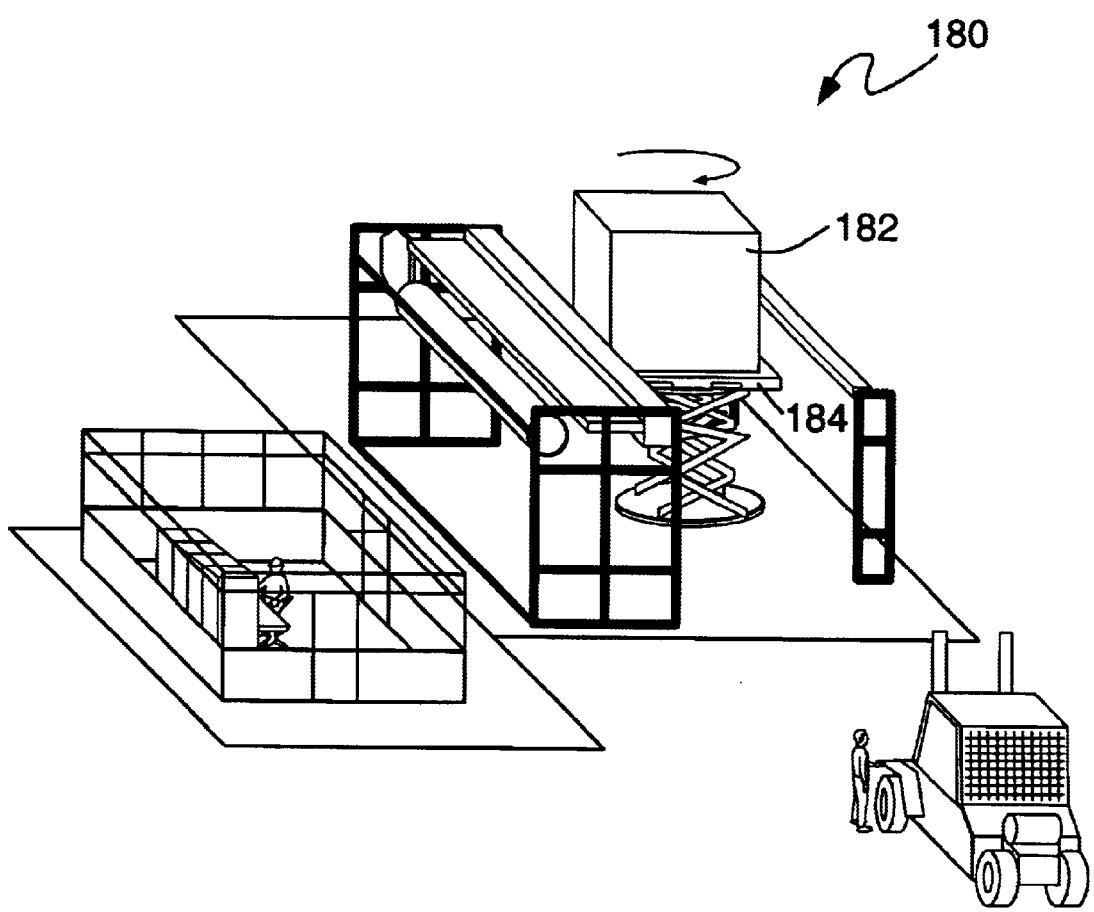
FIG. 10 is a pictorial illustration of a CT inspection system suitable for inspecting air cargo containers 182.

FIG. 10 is a pictorial illustration of a CT inspection system 180 suitable for inspecting air cargo containers 182. The system 180 includes a high energy electron source (e.g., a 1.5 MeV NHVG), which provides an electron beam that is magnetically deflected to scan along a target, generating a scanning x-ray beam. The system 180 provides images of horizontal slices through the pallet as the pallet rotates and the electron beam is translated along the target. In addition, the system 180 includes an elevator 184 that moves the pallet 182 vertically to form additional CT slices.

Figure 11:
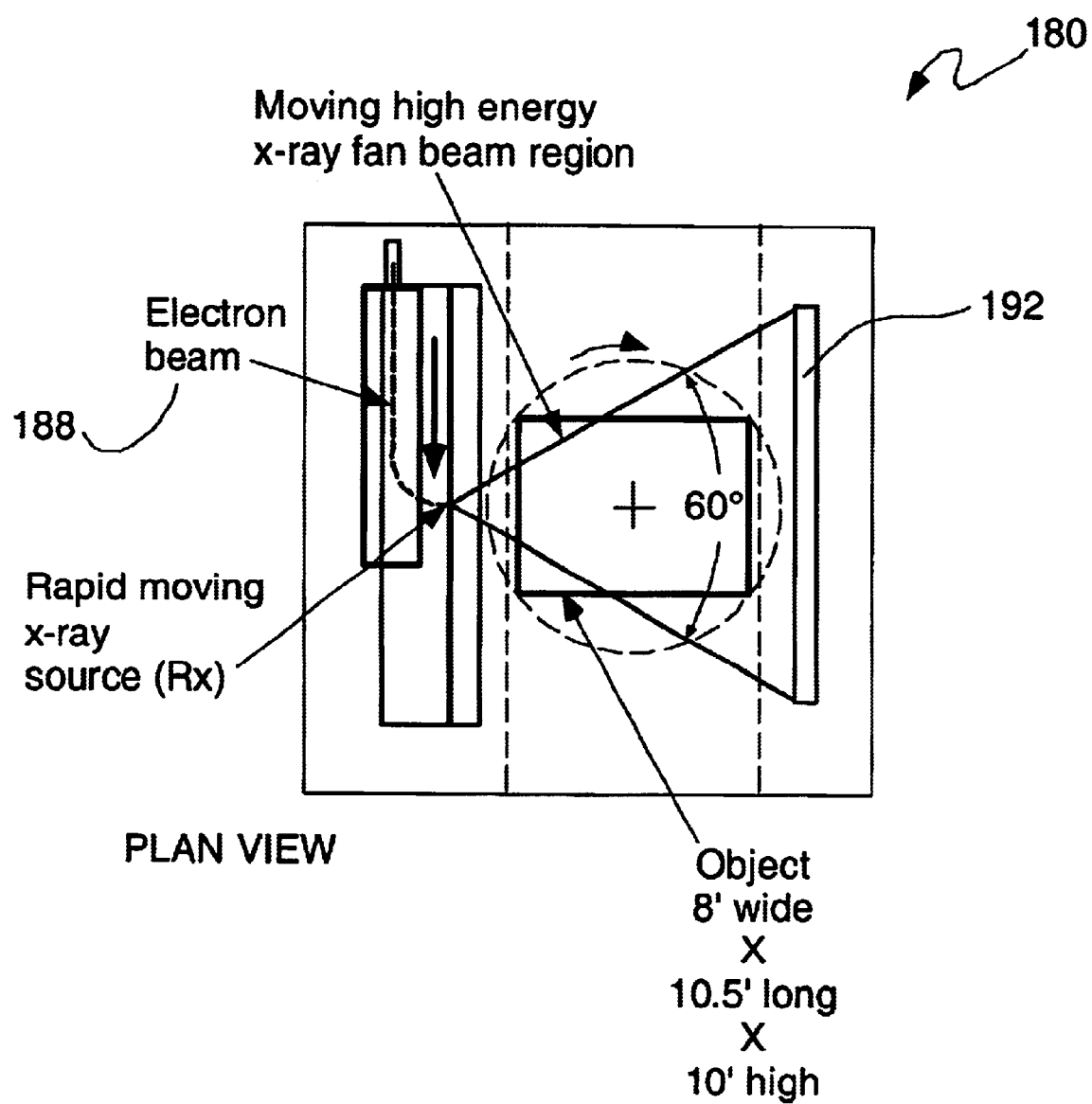
FIG. 11 is a plan view of the CT inspection system illustrated in FIG. 10.
Figure 12:
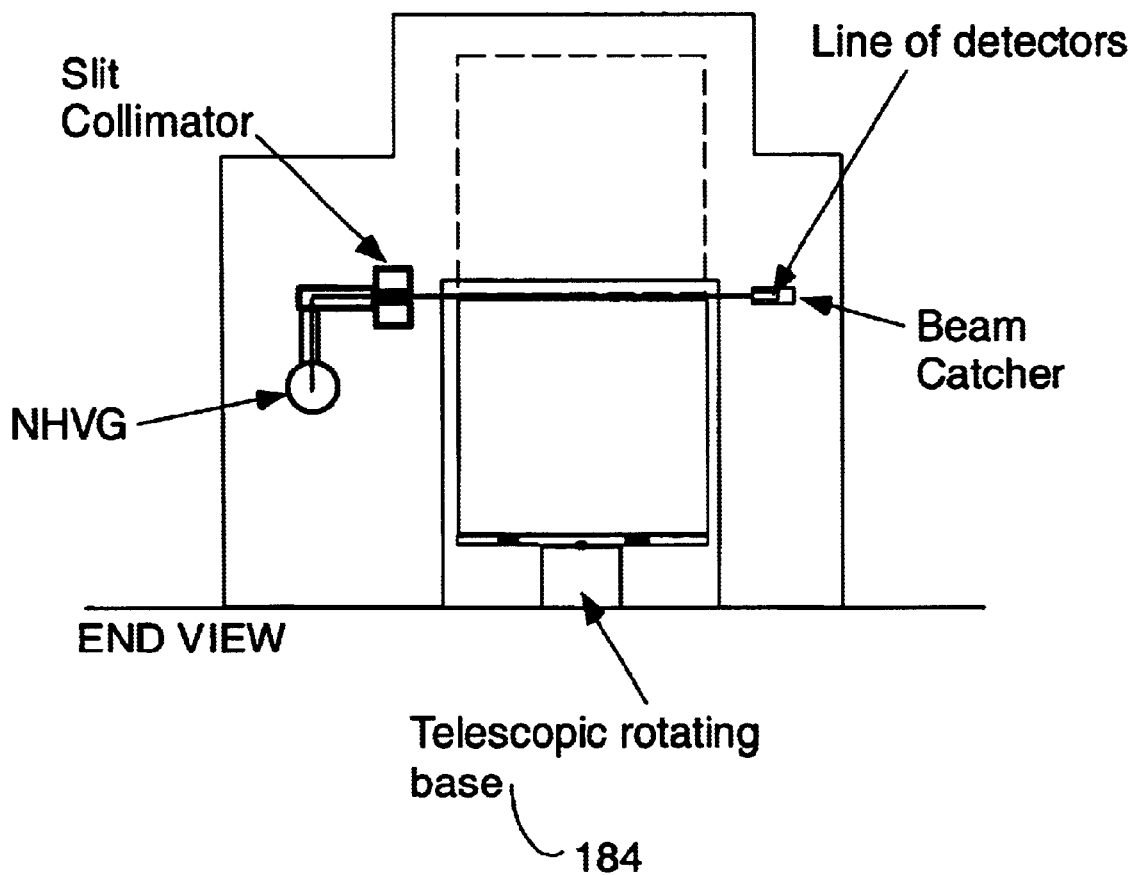
FIG. 12 is an end view of the CT inspection system illustrated in FIGS. 10 and. 11.

FIG. 11 is a plan view of the CT inspection system 180 suitable for inspecting air cargo containers. Electron beam 188 is magnetically deflected to translate along a target to generate a collimated x-ray beam 190. A line to detectors 192 detects the x-rays that pass through he object under inspection, and provide detected signals to a controller/display system (not shown). FIG. 12 is an end view of the CT inspection system 180.

Figure 13:
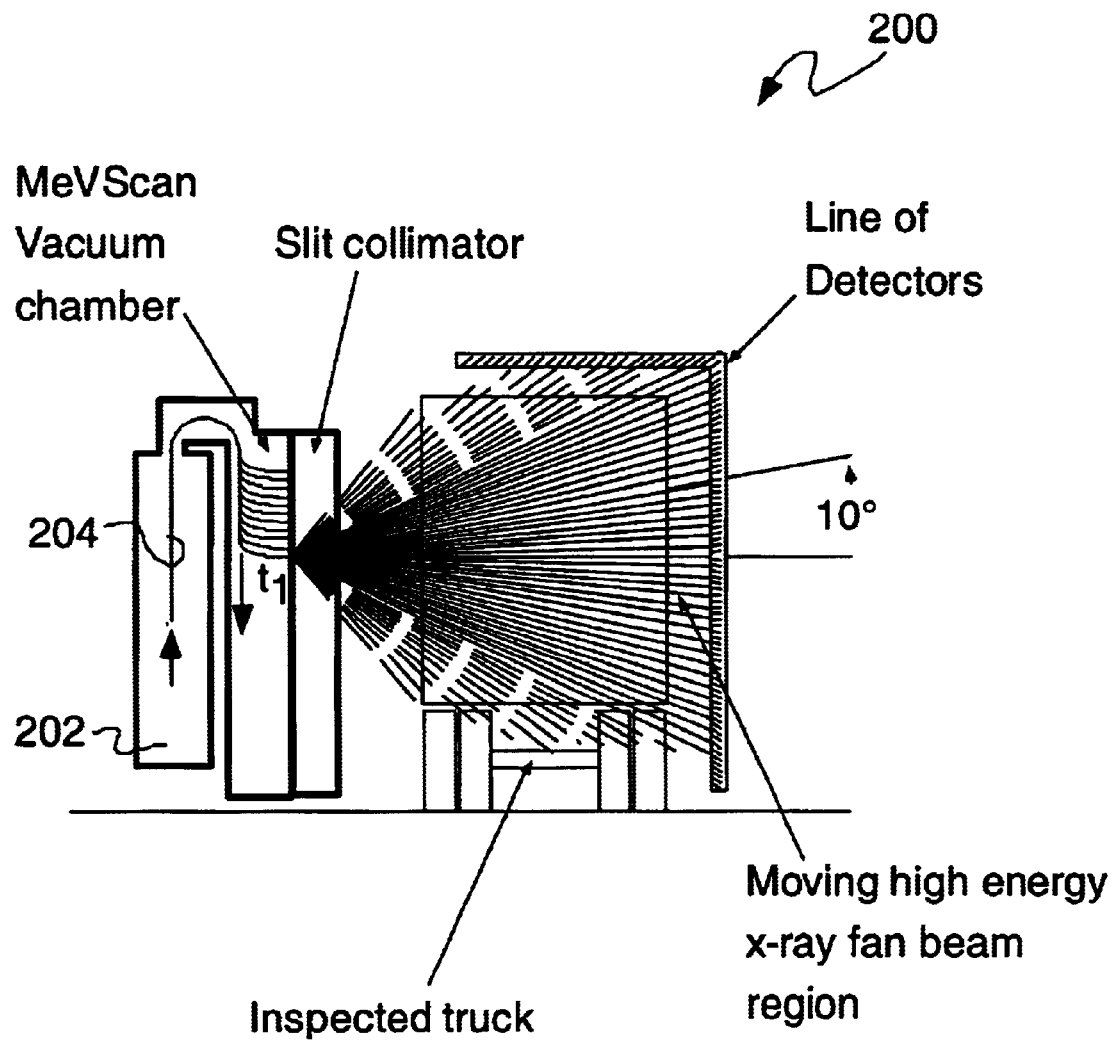
FIG. 13 is an end view of digital tomography x-ray inspection system for inspecting motor vehicles, such as for example trucks.
Figure 14:
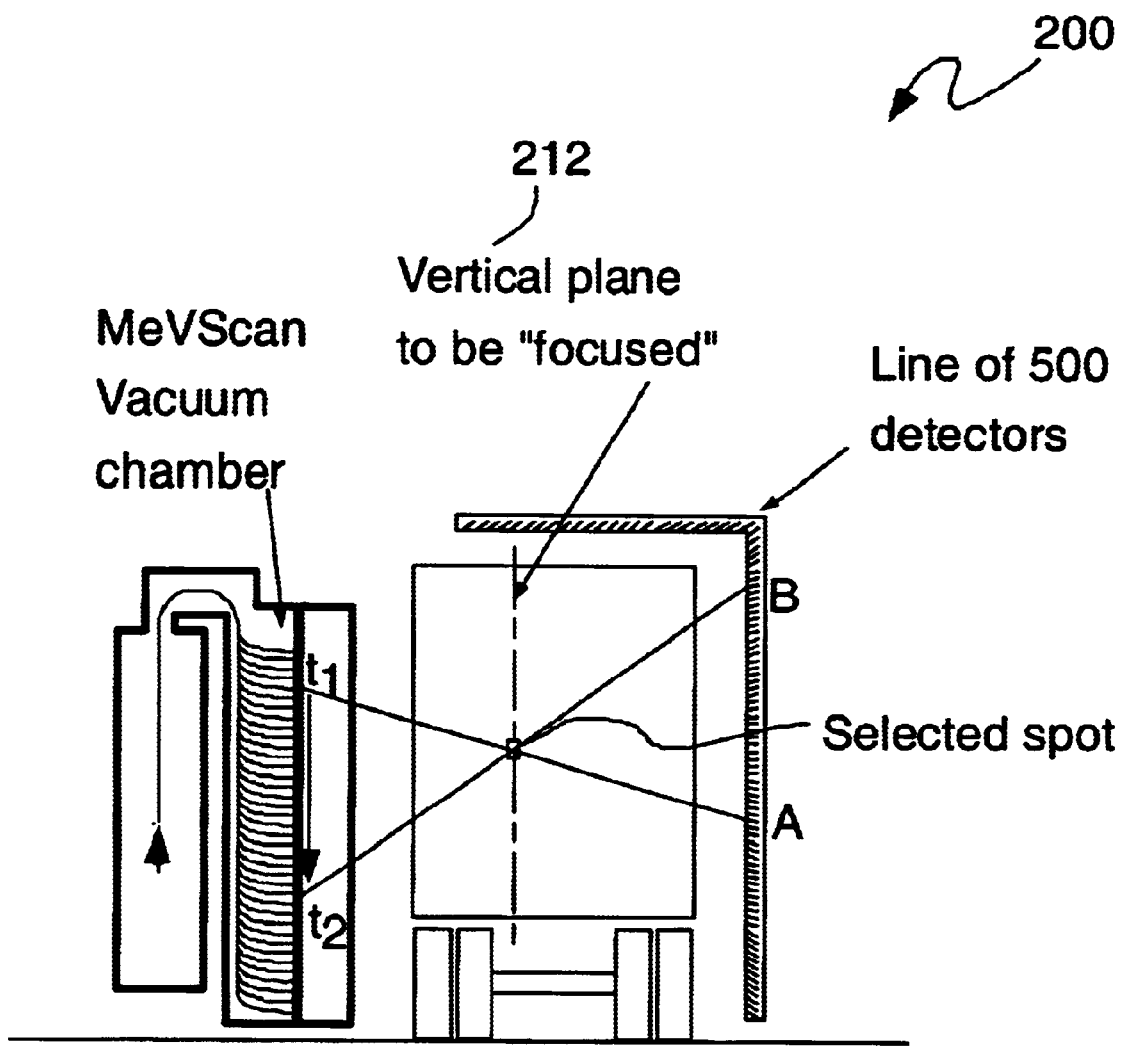
FIG. 14 is a pictorial illustration of an end view of the system illustrated in FIG. 13 illustrating where the electron beam strikes the target at times t1 and t2.

FIG. 13 is an end view of digital tomography x-ray inspection system 200 for inspecting motor vehicles, such as for example trucks. The system includes a high energy electron source 202 that generates an electron beam 204 that is magnetically deflected within a vacuum to translate along a target and generate a cone of x-rays. The cone of x-rays are input to a collimator 206 to provide a fan beam that is vertically scanned. As the electron beam is being translated to form the vertically scanning fan beam, the motor vehicle is being moved through the inspection system. A line of detectors 210 preferably configured as a substantially "L-shaped" detector, detects the x-rays and provides detected signals to a controller/image processor. FIG. 14 is a pictorial illustration of an end view of the system 200 illustrating where the electron beam strikes the target at times t1 and t2, and the associated detectors A and B, respectively, that are used to obtain an image of vertical plane 212 to be focused.

Figure 15:
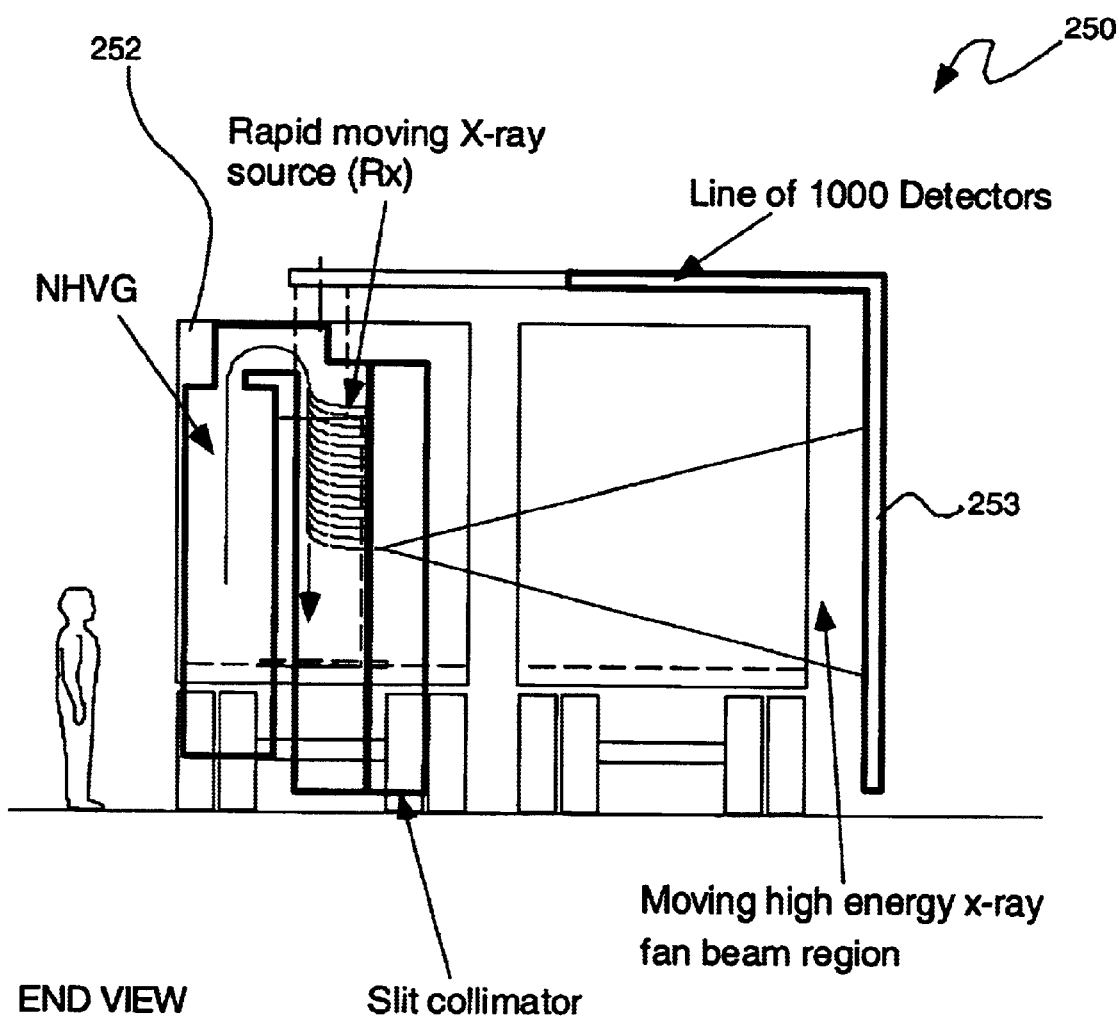
FIG. 15 is a pictorial illustration of a mobile digital tomography x-ray inspection system.
Figure 16:
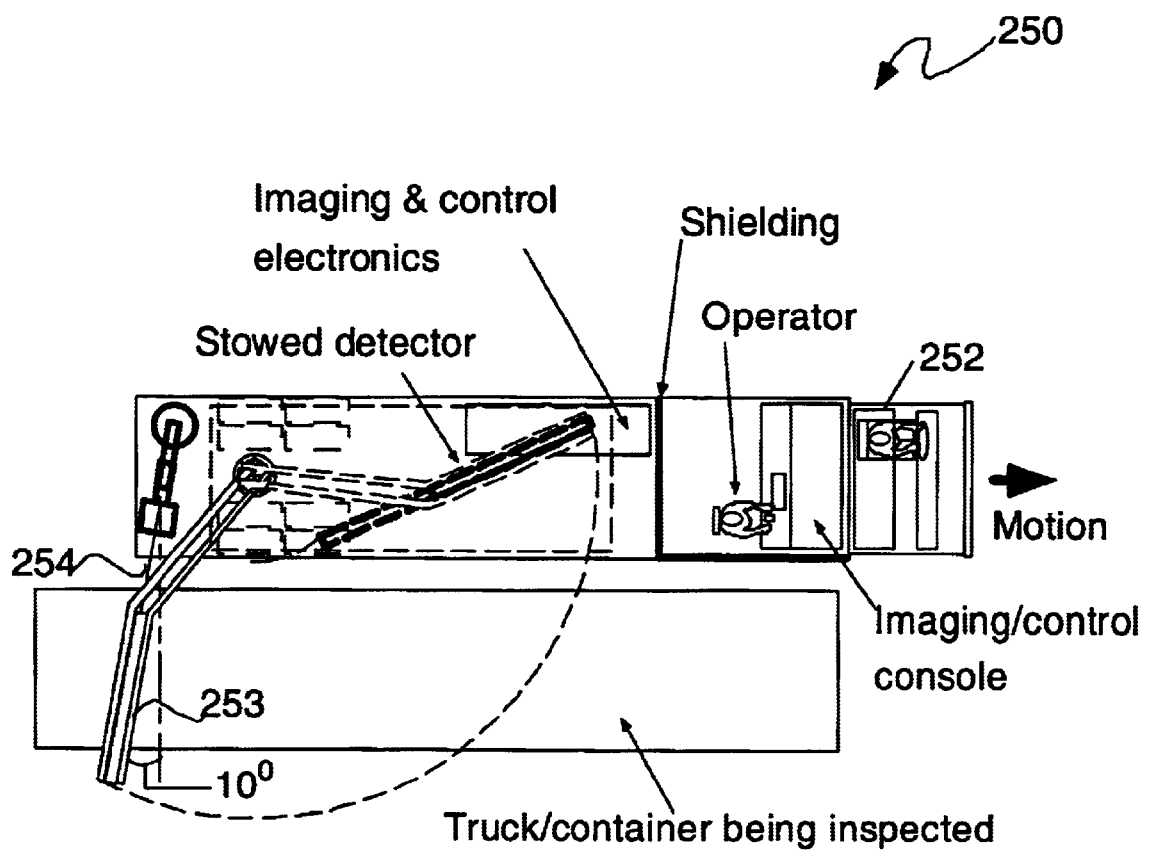
FIG. 16 is a pictorial illustration of a top view of the mobile digital tomography x-ray inspection system illustrated in FIG. 15.
Figure 17:
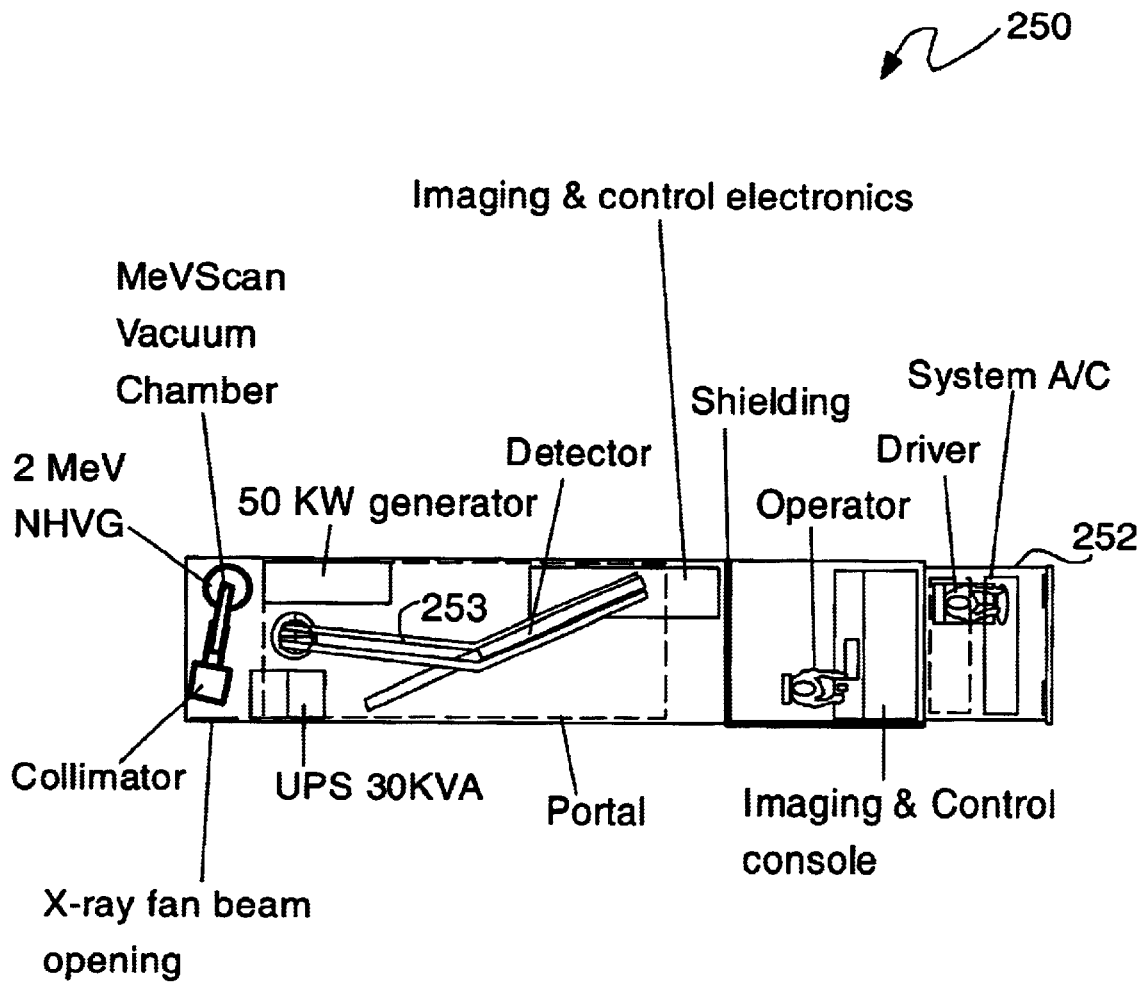
FIG. 17 illustrates an additional plan view illustrating the various components of the mobile system.
Figure 18:
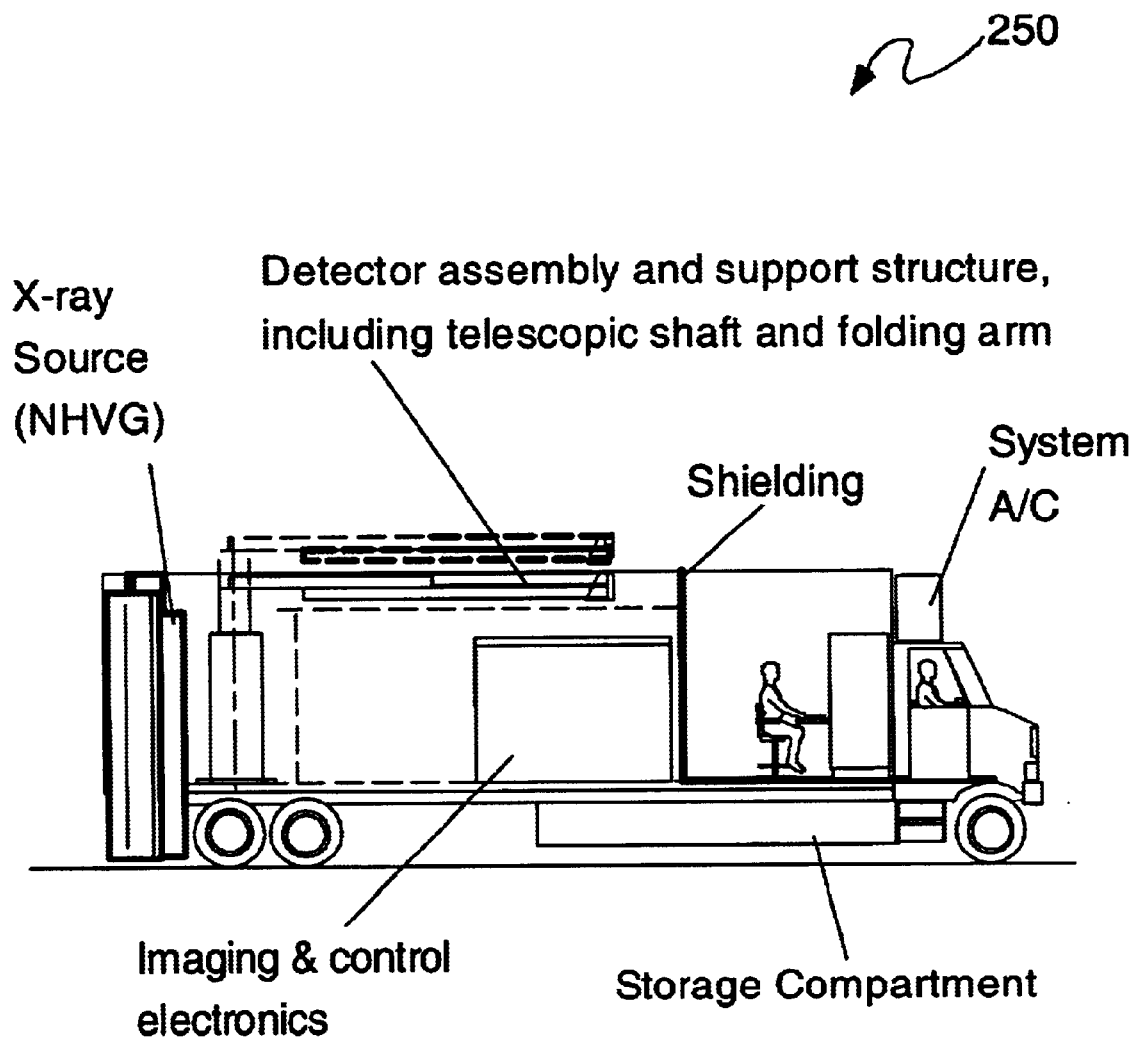
FIG. 18 is a pictorial side view of the mobile system with its components stowed for transport.

Significantly, the digital tomography x-ray inspection system 200 for inspecting motor vehicles may be either a stationary or mobile system. For example, FIG. 15 is a pictorial illustration of a mobile digital tomography x-ray inspection system 250. This system is substantially the same as the system illustrated in FIGS. 12 and 13, except that the system components have been mounted on a transport vehicle 252. FIG. 16 is a pictorial top view of the mobile digital tomography x-ray inspection system 250. The system includes a boom assembly 253 on which the detectors are mounted. The boom 253 is illustrated extending from the transport vehicle 252 and cooperatively positioned with respect to the fan beam 254. The boom 253 is also illustrated in phantom to show the transport position of the boom. FIG. 17 illustrates an additional plan view illustrating the various components of the system. FIG. 18 is a pictorial side view of the system 250 with its components stowed for transport.

Figure 19:
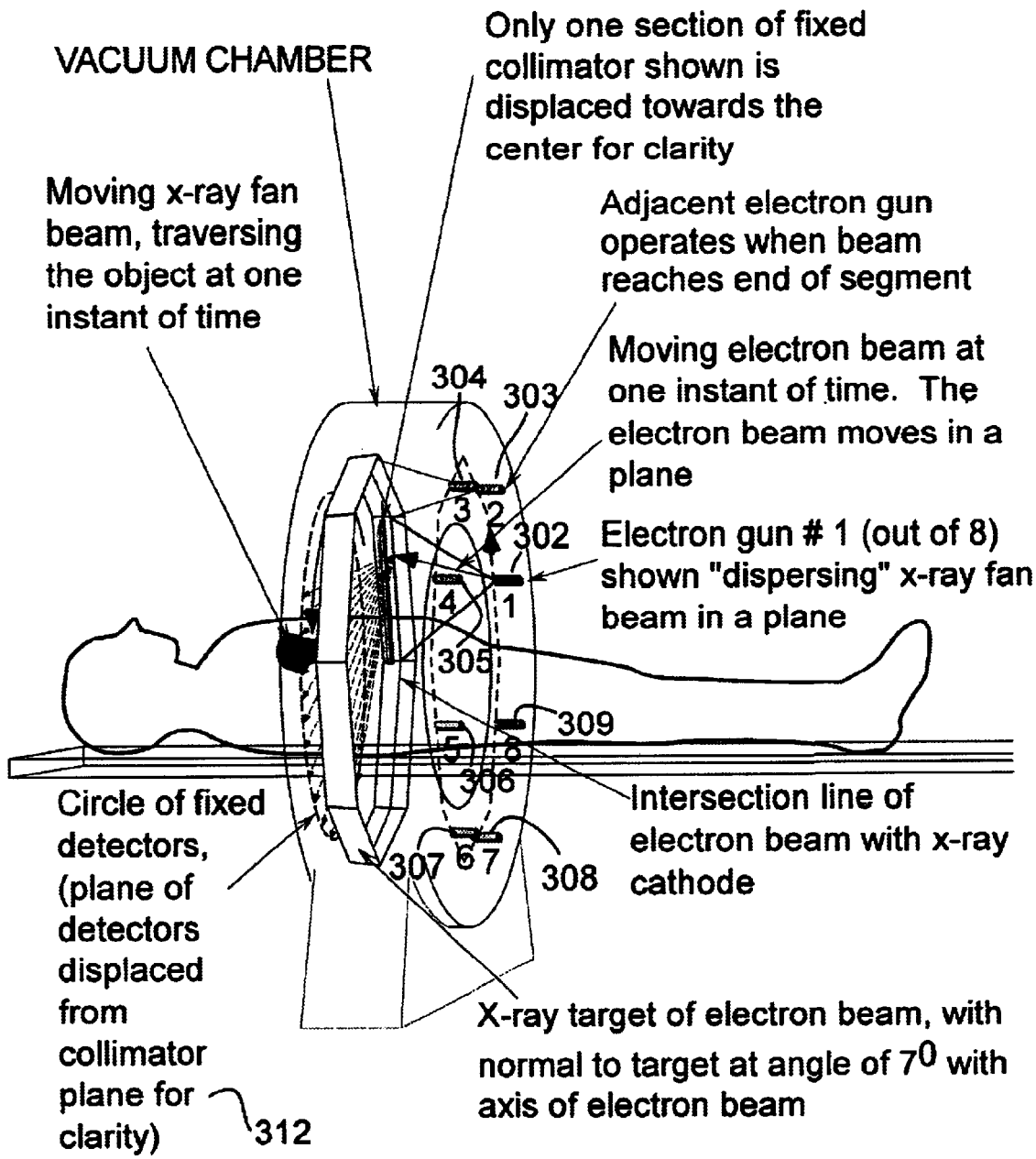
FIG. 19 illustrates a CT imaging system that includes a plurality of sequentially operating x-ray guns.

In another aspect of the invention, FIG. 19 illustrates a CT imaging system 300 that includes a plurality of sequentially operating x-ray guns 302–309 (e.g., eight). Each of the xrays gun assemblies 302–309 is substantially as shown in FIG. 7. Each of the electron gun assemblies produces an high current electron beam that impinges on an associated x-ray cathode, which produces a moving fan beam of x-rays as the electron beam moves rapidly over the cathode in a straight line. When the first electron gun assembly 302 has traversed its associated cathode, the power is switched to the second electron gun 303 which continues to form the x-ray fan beam encircling the object under inspection. Similarly, once the second electron gun assembly 303 has traversed its associated cathode, the power is switched to the third electron gun 304 which continues to form the x-ray fan beam encircling the object under inspection. The electron gun assemblies 302–309 are sequentially operated to form the desired image.

In one embodiment, each source may be about 18 inches above its associated cathode. Advantageously, this avoids spreading of the electron beam caused by coulomb repulsion between the electrons. This coulomb repulsion is worse as the beam length increases, hence the value of the short beam length. The fan beam of the x-rays is aimed slightly out of the plane of the paper so that it will intersect the array of fixed detectors, which are placed adjacent to the vacuum chamber. Of course the system also includes an associated detector assembly 312.

Although each of the systems disclosed herein has a different application, each system has the common feature of an x-ray source that generates an electron beam that is rapidly deflected along a target material to generate the requisite penetrating X-rays.

Although the present invention has been shown and described with respect to several preferred embodiments thereof, various changes, omissions and additions to the form and detail thereof, may be made therein, without departing from the spirit and scope of the invention.

What is claimed is:

1. A digital tomography system, comprising:
   an electron source that provides a pencil beam of electrons;
   an electromagnet assembly that receives said pencil beam of electrons and is configured and arranged to direct said beam of electrons along a selected path, to bend said pencil beam of electrons and to scan the bended electron beam along a line to form a scanning redirected beam;
   a linear target that is struck by said scanning redirected beam of electrons and generates a cone of x-rays that moves along a target line as a result of said scanning redirected beam;
   a slit collimator that receives said scanning cone of x-rays and generates a scanning fan beam, which are directed to an object under inspection, wherein each point in the object under inspection receives x-rays from various angles;
   a first line of detectors positioned in the same plane as the linear target to detect xrays that pass through the object under inspection, and provide sensed signals indicative thereof; and
   a processing system that receives said sensed signals and forms a digital tomographic image of selected planes through the object under inspection.

2. The digital tomography system of claim 1, wherein said electron source includes a high voltage electron accelerator.

3. The digital tomography system of claim 1, wherein said electron source includes a nested high voltage electron generator.

4. The digital tomography system of claim 1, wherein said first line of detectors includes a plurality of photo multiplier tubes.

5. The digital tomography system of claim 1, further comprising a second line of detectors and a third line of detectors, each perpendicular to said first line of detectors, wherein said first, second and third line of detectors form a U-shaped detector configured and arranged to detect x-rays that pass through the object under inspection.

6. The digital tomography system of claim 1, said first line of detectors includes a plurality of solid state detectors.

7. A computed tomography system, comprising:
   means for providing a pencil beam of electrons;
   means for receiving said pencil beans of electrons, for directing said beam of electrons along a selected path, and for bending said pencil beam of electrons and for scanning said bended electron beam along a line to form a scanning redirected beam;
   a linear target that is struck by said scanning redirected beam of electrons and generates a cone of x-rays that moves along a target line as a result of said scanning redirected beam;

a collimator that receives said scanning cone of x-rays and generates a scanning fan beam directed to an object under inspection, wherein each point in the object under inspection receives x-rays from at least 180 degrees about the object under inspection;

a line of detectors positioned in the same plane as the linear target to detect x-rays that pass through the object under inspection, and provide sensed signals indicative thereof; and a processing system that receives said sensed signals and forms a computed tomography image of selected planes through the object under inspection.

8. The computed tomography system of claim 7, further comprising a platform that moves laterally and rotates, and onto which the object under inspection is placed.

9. The computed tomography system of claim 7, wherein said means for providing a pencil beam of electrons is separated from said linear target by about 18 inches.

10. A computed tomography system, comprising:

a plurality of x-ray sources arranged around an object under inspection, each of said x-ray sources including
 (i) means for providing a pencil beam of electrons;
 (ii) an electromagnet assembly that receives said pencil beam of electrons and is configured and arranged to direct said beam of electrons along a selected path and bend said pencil beam of electrons and scans the bended electron beam along a line to form a scanning redirected beam;
 (iii) a linear target that is struck by said scanning redirected beam of electrons and generates a cone of x-rays that moves along a target line as a result of said scanning redirected beam;
 (iv) a slit collimator that receives said scanning cone of x-rays and generates a scanning fan beam directed to an object under inspection, wherein said plurality of x-ray sources surround the object under inspection such that the object receives x-rays from at least 180 degrees about the object under inspection;

lines of detectors positioned to detect x-rays that pass through the object under inspection, and provide sensed signals indicative thereof; and a computing device that receives said sensed signals to form a computed tomography image of the object under inspection.

11. The computed tomography system of claim 10, wherein said detectors comprise a plurality of substantially U-shaped detectors that detect x-rays from each of said x-ray sources, wherein each of said U-shaped detectors includes first and second parallel detector arms separated by a perpendicular detector arm, each including a plurality of photodetective elements.

12. The computed tomography system of claim 10, further comprising a platform that moves laterally and rotates, and onto which the object under inspection is placed.

13. The computed tomography system of claim 10, wherein the object under inspection includes luggage.

14. The computed tomography system of claim 10, wherein each means for providing a pencil beam of electrons is separated from its associated linear target by about 18 inches.

* * * * *